United States Patent
Sun

(10) Patent No.: US 9,518,142 B2
(45) Date of Patent: Dec. 13, 2016

(54) PROCESS FOR PREPARING ISOCYANATE HOMOPOLYMERS CONTAINING URETDIONE GROUPS

(71) Applicants: Wanhua Chemical (Ningbo) Co., Ltd., Ningbo (CN); Wanhua Chemical Group Co., Ltd., Yantai (CN)

(72) Inventor: Lidong Sun, Ningbo (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 14/907,153

(22) PCT Filed: Mar. 3, 2014

(86) PCT No.: PCT/CN2014/072798
§ 371 (c)(1),
(2) Date: Jan. 22, 2016

(87) PCT Pub. No.: WO2015/078116
PCT Pub. Date: Jun. 4, 2015

(65) Prior Publication Data
US 2016/0159964 A1 Jun. 9, 2016

(30) Foreign Application Priority Data
Nov. 26, 2013 (CN) .......................... 2013 1 0608843

(51) Int. Cl.
*C08G 18/02* (2006.01)
*C08G 18/16* (2006.01)
*C07F 9/54* (2006.01)

(52) U.S. Cl.
CPC ........... *C08G 18/027* (2013.01); *C07F 9/5414* (2013.01); *C08G 18/168* (2013.01)

(58) Field of Classification Search
CPC ..... C08G 18/027; C08G 18/168; C07F 9/5414
See application file for complete search history.

(56) References Cited

U.S. PATENT DOCUMENTS

| 8,134,014 B2 | 3/2012 | Richter et al. |
|---|---|---|
| 2004/0106789 A1 | 6/2004 | Richter et al. |
| 2005/0113551 A1 | 5/2005 | Richter et al. |
| 2008/0262262 A1 | 10/2008 | Richter et al. |
| 2009/0143558 A1 | 6/2009 | Richter et al. |
| 2010/0152489 A1 | 6/2010 | Mayama |

FOREIGN PATENT DOCUMENTS

| CN | 1502605 A | 6/2004 |
|---|---|---|
| CN | 1660792 A | 8/2005 |
| CN | 101289427 A | 10/2008 |
| CN | 101450928 A | 6/2009 |
| CN | 101747377 A | 6/2010 |
| CN | 102942525 A | 2/2013 |
| CN | 103613540 A | 3/2014 |
| DE | 1670720 A1 | 1/1971 |
| WO | 2011126045 A1 | 10/2011 |
| WO | 2015078116 A1 | 6/2015 |

OTHER PUBLICATIONS

Imamoto et al., "Synthesis and reactions of phosphine-boranes. Synthesis of new bidentate ligands with homochiral phosphine centeres via optically pure phosphine-boranes", J. Am. Chem. Soc. 1990, 112, 5244-5252.
International Search Report for Application No. PCT/CN2014/072798 dated Aug. 20, 2014.
Overschelde et al., "Catalyst-free alcoholysis of phosphane-barones: a smooth, cheap, and efficient deprotection procedure", Tetrahedron 65 (2009) 6410-6515.

*Primary Examiner* — Rabon Sergent
(74) *Attorney, Agent, or Firm* — Lerner, David, Littenberg, Krumholz & Mentlik, LLP

(57) ABSTRACT

The present invention relates to a process for preparing isocyanate homopolymers containing uretdione groups, in which the phosphinoboron compound of formula (I) are used as catalysts to catalyze the homopolymerization reaction of raw isocyanates, thereby obtaining a solution of isocyanate homopolymers having uretdione groups, then separating the solution and thus obtaining the isocyanate homopolymers containing uretdione groups. The isocyanate homopolymers containing uretdione groups prepared by this process have a high amount of the uretdione groups, wherein the dependence of the amount on the conversion rate of raw isocyanates is significantly ameliorated, with low chromaticities.

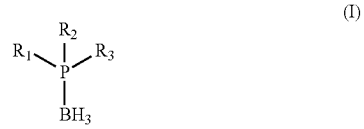

(I)

19 Claims, No Drawings

PROCESS FOR PREPARING ISOCYANATE HOMOPOLYMERS CONTAINING URETDIONE GROUPS

FIELD OF THE INVENTION

The present invention relates to a process for preparing isocyanate homopolymers with a high uretdione group content.

BACKGROUND OF THE INVENTION

Isocyanate homopolymers containing uretdione groups have a particularly low viscosity, thus, as crosslinkers, they have relatively good applicabilities in coating compositions with low solvent and a high solid content.

The key in preparation of isocyanate homopolymers with a high uretdione group content is to select catalysts. Catalysts reported in patents mainly include tertiary phosphine compounds, boron trifluoride compounds, and pyridine compounds.

DE 1670720 discloses a process for preparing isocyanate homopolymers containing uretdione groups by using at least one aliphatically substituted tertiary phosphine or boron trifluoride compound. The isocyanate homopolymers obtained by this process have a relatively high uretdione content, however, the conversion rate thereof is low.

The preparation of polyisocyanates containing uretdione groups are disclosed in CN 1502605 and CN 1660792, in both of which the catalysts used are tertiary phosphines containing cycloalkyl substituent or directly phosphorus-attached cycloalkyl substituent. The imperfection lies in that the content of uretdione group highly depends on the conversion rate in the preparation of isocyanate homopolymers containing uretdione groups. In another word, isocyanate homopolymers with a high uretdione group content can be only obtained under the condition of relatively low conversion rate of isocyanate. Accordingly, a large amount of unreacted raw isocyanate monomers are required to be recovered in the product separation stage, thereby rendering a high processing energy cost.

U.S. Pat. No. 8,134,014 discloses a process for preparing polyisocyanates containing uretdione group, in which the catalysts used are aminopyridine compounds substituted by fused ring(s). The prepared isocyanate homopolymers have a relatively high uretdione group content, and there is no special limitation on the applicable isocyanates. However, the pyridine compounds used tend to color the products. As a result, there is still a need of developing specific processes, wherein the contents of uretdione groups are high with less dependence on the conversion rate of raw isocyanates, and the chromaticity of products as well as the cost of processing energy is low.

SUMMARY OF THE INVENTION

The object of present invention is to provide a process for preparing isocyanate homopolymers containing uretdione groups, in which the phosphinoboron compounds are used as catalysts to catalyze isocyanate homopolymerization, thereby preparing isocyanate homopolymers containing uretdione groups. The isocyanate homopolymers obtained in this process have a high uretdione group content, with an obvious ameliorated dependence on the convention rate of the raw isocyanates, and the chromaticity of products is low as well as the cost of processing energy is prominently reduced.

In order to achieve the aforementioned purposes, the present invention adopts the following technical solutions:

A process for preparing isocyanate homopolymers containing uretdione groups, which includes:

in the presence of catalysts, homopolymerizing at least one kind of the raw isocyanates to prepare isocyanate homopolymers containing uretdione groups, wherein the catalysts are phosphinoboron compounds with the structure of formula (I):

where, $R_1$, $R_2$ and $R_3$ are independently selected from linear or branched $C_1$-$C_{20}$ alkyl group, optionally substituted $C_3$-$C_{20}$ cycloalkyl group, optionally substituted $C_7$-$C_{15}$ aralkyl group or optionally substituted $C_6$-$C_{12}$ aryl group; and wherein the term "optionally substituted" refers to the group can be substituted by single or multiple substituent(s) selected from $C_1$-$C_{10}$ alkyl group, $C_1$-$C_{10}$ alkoxyl group, $C_6$-$C_{12}$ aryl group or $C_7$-$C_{15}$ aralkyl group; or unsubstituted.

Preferably, $R_1$, $R_2$ and $R_3$ are independently selected from methyl, linear or branched $C_3$-$C_{20}$ alkyl group, alkyl-substituted $C_3$-$C_{20}$ cycloalkyl group, alkyl-substituted $C_7$-$C_{15}$ aralkyl group, alkyl-substituted $C_6$-$C_{12}$ aryl group or alkoxyl-substituted $C_6$-$C_{12}$ aryl group; wherein, the alkyl substituents are selected from $C_1$-$C_{10}$ linear or branched alkyl group, and the alkoxyl substituents are selected from $C_1$-$C_{10}$ alkoxyl group.

More preferably, $R_1$, $R_2$ and $R_3$ are independently selected from methyl, n-butyl, tert-butyl, cyclopropyl, cyclohexyl, phenyl or methoxyphenyl.

The phosphinoboron compound catalysts of formula (I) in the present invention are preferably selected from one, two or more of the following catalysts:

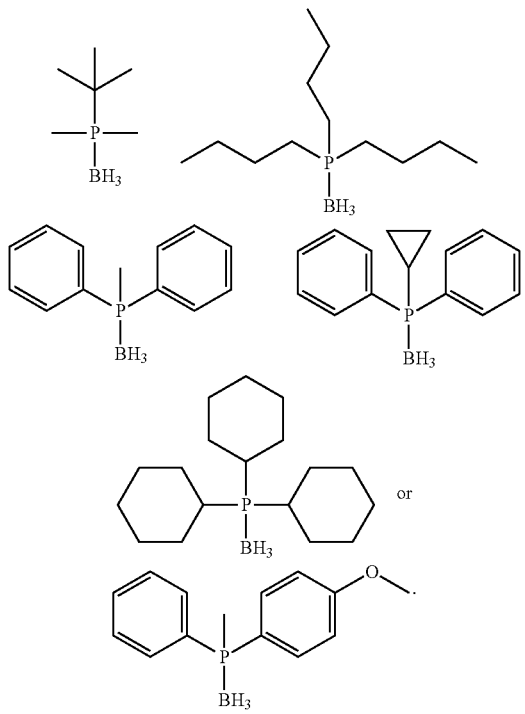

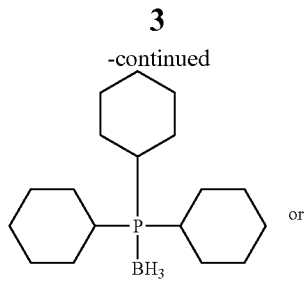

The raw isocyanate monomer of the present invention is selected from one of the following compounds: aliphatic isocyanate, cycloaliphatic isocyanate or aromatic isocyanate; wherein the isocyanate having a NCO functionality ≥2.

For instance, the raw isocyanate monomers of the present invention are preferably selected from one of the following compounds: tetramethylene-1,4-diisocyanate, pentamethylene-1,5-diisocyanate, hexamethylene-1,6-diisocyanate, lysine diisocyanate, isophorone diisocyanate, trimethylhexamethylene diisocyanate, dicyclohexylmethane diisocyanate, norbornane dimethylene isocyanate, diphenylmethane diisocyanate, toluene diisocyanate or p-phenyl diisocyanate. More preferably, they are selected from hexamethylene-1,6-diisocyanate or isophorone diisocyanate.

The amount of phosphinoboron compound catalyst in accordance with formula (I) used in the present invention is 0.1-4 mol % of the amount of raw isocyanate monomer, preferably is 0.5-2 mol %, based on the mole amount of raw isocyanate monomers.

The phosphinoboron compound catalysts of formula (I) in the present invention can be used solely or as a formulated solution, wherein the concentration of the formulated solution is 0.5-5 mol/L, preferably 2-4 mol/L; and the solvents used in formulating the solution are free of the active hydrogen; preferably, one, two or more of halogenated hydrocarbons, aromatic hydrocarbons or ethers; more preferably, one, two or more of dichloromethane, tetrahydrofuran, methylbenzene, dimethylbenzene or chlorobenzene.

In the present invention, the temperature of the homopolymerization reaction of the raw isocyanate monomers is 20-120° C., preferably, 50-100° C.

In the process of the present invention, when the conversion rate of isocyanates reaches 20%-60% (based on the mass of raw isocyanate monomers), the homopolymerization reaction is terminated by using catalyst poisons. The catalyst poisons can be the known alkylating agents including dimethyl sulphate, methyl p-toluenesulphonate etc.; or phosphate esters including dimethyl phosphate, diethyl phosphate, di-n-butyl phosphate and so on. The mole ratio of the catalyst poison to the catalyst is 1:1-2:1; preferably 1:1-1.2:1.

At a suitable temperature, the phosphinoboron compound catalysts of formula (I) according to the present invention with a molecule of isocyanate can firstly form a transition state of four-membered ring structure having the structure of formula II, and further activate the carbon atom of NCO function group in the raw isocyanates, thereby rendering more liable to bond with another molecule of isocyanate, and can further result in a transition state as a six-membered ring structure of formula III. Since the transition state of the six-membered ring is relatively stable, its ratio is higher than every other intermediate transition state during the polymerization process of isocyanates (during the polymerization process, there are transition states of nine-membered rings for forming isocyanurate and iminooxadiazindione, i.e. formulae IV and V), it is the primary intermediate transition state. Accordingly, after the catalysts of the transition states of formulae III, IV and V are removed, the uretdione, isocyanurate and iminooxadiazindione are obtained, respectively, wherein the uretdione accounts for the main part.

In order to illustrate clearly, the homopolymerization process is described in the following formulae, wherein OCN—R—NCO denotes the raw isocyanate monomer, CAT represents the catalysts with the structure of formula (I).

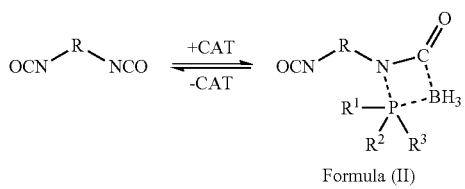

Formula (II)

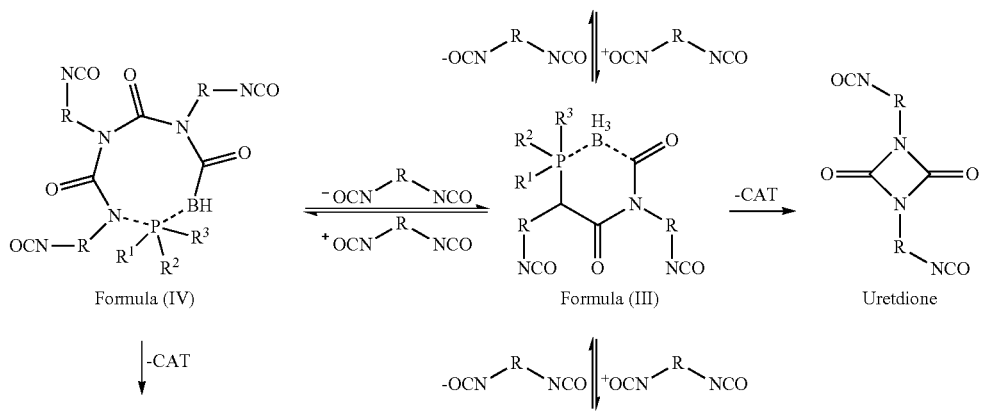

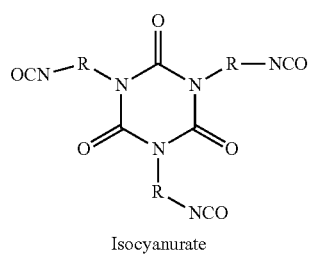

Isocyanurate

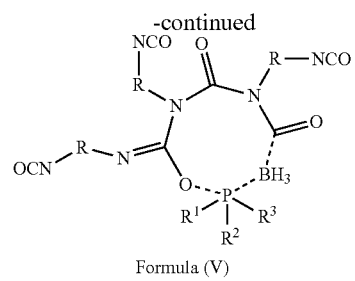

Formula (V)

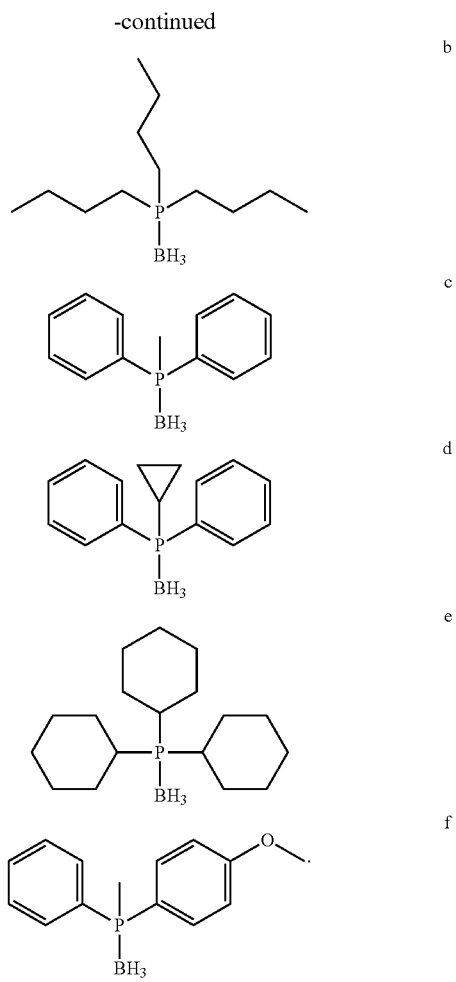

Iminooxadiazindione

According to the process of the present invention, using the phosphinoboron compounds of the present invention as catalysts can effectively catalyze the homopolymerization reaction of raw isocyanate monomers to prepare polyisocyanates with a high uretdione group content. Compared with the preparation processes by using the catalysts in the art, the process of the present invention achieves a higher conversion rate of raw isocyanates as well as a higher uretdione content in the product. Meanwhile, lower chromaticity can be obtained via preparing the polyisocyanates by using phosphinoboron compounds of formula (I) according to the present invention as catalysts.

DETAILED DESCRIPTION OF THE PREFERRED EMBODIMENTS

The process provided by the present invention would be further illustrated by the following embodiments, but the present invention is not limited to these embodiments.

Gel chromatography (LC-20AD/RID-10A, columns: MZ-Gel SDplus 10E3A 5 μm (8.0×300 mm), MZ-Gel SDplus 500A 5 μm (8.0×300 mm), MZ-Gel SDplus 100A 5 μm (8.0×300 mm) in series, Shimadzu; mobile phase: tetrahydrofuran; flow rate: 1.0 mL/min; retention time: 40 min, column temperature: 35° C.) is applied to quantify the isocyanate monomers, which is used as a monitoring manner to determine the reaction conversion rate (based on the mass of raw isocyanate monomers).

The mole ratio of uretdione-containing polymers to the sum of other polymer components (i.e. the sum of polyisocyanates and polyiminooxadiazindione) in the resulted polyisocyanate homopolymers in the examples and the comparative examples is denoted as U/O. The measurement of U/O value referenced to the method described in CN101289427, wherein the $^{13}$C-NMR is applied. The instrument used is Bruker 400 MHz, the concentration of sample is 50% (CDCl$_3$ solution), testing condition is 100 MHz, relaxation time: 4 sec, 2000 scans/min, δ=77.0 ppm of CDCl$_3$ is taken as the reference of chemical shift.

BYK LCS III is chosen as a colorimeter, with 50 mm sample cell, pure water (0 Hazen) is used as a reference.

All reactant solutions are under an atmosphere of dry nitrogen before the reaction starts to the addition of catalysts and during the whole reaction process, unless specifically noted otherwise.

Catalysts involved in the examples of the present invention are selected from:

a

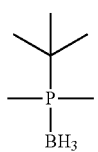

Wherein catalyst a was purchased from Sigma-Aldrich; catalyst b was prepared according to the process of the reference (Tetrahedron, 2009, 65, 6410-6415); catalyst c, d and f were prepared in accordance with the method described in the reference (J. Am. Chem. Soc, 1990, 112, 5244-5252); catalyst e was prepared according to the process of the reference (Tetrahedron, 2009, 65, 6410-6415).

For example, the process for preparing catalyst b was as follows:

1) At room temperature, 100 ml CH$_2$Cl$_2$ and 10 mmol tertiary phosphine were added into a 250 mL three necked flask under the nitrogen atmosphere, and the reactants were started to stir;
2) The reaction was stirred for 10 min before adding 100 ml BH$_3$SMe$_2$ solution (1 mol/L in SMe$_2$), then stirred for 24 h at room temperature;

3) 50 ml saturated ammonium chloride solution was added in the flask, after stirring for 10 min, all of the solution in the flask was poured into a separatory funnel containing 100 ml pure water, and extracted with $CH_2Cl_2$ for three times. The organic phase was washed with saturated sodium bicarbonate solution, and dried with dry magnesium sulfate for 24 h;
4) The solution was vacuum filtrated to remove the solid magnesium sulfate after dryness, then the filtrate was concentrated with a rotary evaporator;
5) After concentrating, the solution was separated and purified by silica-gel column chromatography using $CH_2Cl_2$ as a eluent;
6) The resulted 7 mmol solid catalyst b was formulated into an 0.5 mol/L of $CH_2Cl_2$ solution for use.

The catalysts in the comparative examples were selected from g and h with the following structures reported in the patent documents, i.e. CN 1502605 and CN 101450928, respectively:

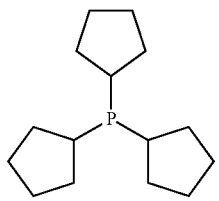

g

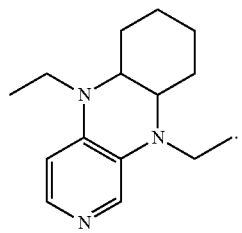

h

EXAMPLES 1-6

The general experimental steps of examples 1-6 are as follows:

To a four-necked flask containing 1680 g (10 mol) hexamethylene-1,6-diisocyanate (HDI) at 55° C. was added a certain amount of catalysts with stirring, and timing was started. During the reaction, the temperature was maintained between 55° C. and 65° C., the HDI was quantified by the gel chromatography to monitor the conversion rate of reaction. Once the required conversion rate was achieved, a certain amount of terminating agent was added to cease the reaction. After the reaction was finished, separation was conducted and a light colored HDI homopolymer with a high uretdione content was obtained. Detail conditions are listed in table 1.

TABLE 1

Experimental Conditions of Examples 1-6

| | Catalyst | Catalyst Amount (based on the amount of HDI, mol %) | Using Condition | Solution and Concentration (mol/L) | Terminating Agent | Amount of Terminating Agent (mol) |
|---|---|---|---|---|---|---|
| Example 1 | a | 0.1 | Solid | — | diethyl phosphate | 0.01 |
| Example 2 | b | 0.5 | Solution | 5 (dichloromethane) | | 0.05 |
| Example 3 | c | 1 | Solution | 4 (dichloromethane) | | 0.12 |
| Example 4 | d | 2 | Solution | 2 (tetrahydrofuran) | | 0.24 |
| Example 5 | e | 2 | Solid | — | | 0.20 |
| Example 6 | f | 3 | Solution | 0.5 (tetrahydrofuran) | | 0.30 |

COMPARATIVE EXAMPLE 1

Referring to the process of CN 1502605, the process is similar to example 1, except using 0.12 mol catalyst g in catalyzing the homopolymerization reaction and 0.14 mol diethyl phosphate in terminating the reaction.

COMPARATIVE EXAMPLE 2

Referring to the process of CN 101450928, the process is similar to example 1, except using 0.24 mol catalyst h in catalyzing the homopolymerization reaction and 0.24 mol diethyl phosphate in terminating the reaction.

TABLE 2

U/O Values of the HDI Homopolymers Prepared in Examples 1-6 and Comparative Examples 1-2

| | U/O U/O Values of the Prepared HDI Homopolymers | | | | | | | |
|---|---|---|---|---|---|---|---|---|
| Conversion Rate | Example 1 | Example 2 | Example 3 | Example 4 | Example 5 | Example 6 | Comparative Example 1 | Comparative Example 2 |
| 20% | 53.1 | 52.2 | 54.6 | 55.6 | 57.1 | 55.4 | 32.6 | 47.2 |
| 30% | 42.3 | 41.4 | 43.5 | 44.6 | 46.8 | 43.5 | 12.3 | 33.3 |

TABLE 2-continued

U/O Values of the HDI Homopolymers Prepared in Examples 1-6 and Comparative Examples 1-2

U/O Values of the Prepared HDI Homopolymers

| Conversion Rate | Example 1 | Example 2 | Example 3 | Example 4 | Example 5 | Example 6 | Comparative Example 1 | Comparative Example 2 |
|---|---|---|---|---|---|---|---|---|
| 45% | 31.7 | 31.2 | 33.5 | 35.1 | 37.7 | 33.4 | 7.8 | 20.6 |
| 60% | 20.3 | 20.1 | 22.7 | 23.0 | 24.5 | 22.3 | 4.4 | 9.1 |

All content ratios of uretdione to other polymer components (U/O values) in the HDI homopolymers prepared by the catalysts (examples 1-6) of the present invention are totally higher than those of the comparative examples; furthermore, as the conversion rate increases from 20% to 60%, the decrease of U/O value is obviously smaller than those in the comparative examples.

TABLE 3

Chromaticity of the HDI Homopolymers Prepared in Examples 1-6 and Comparative Examples 1-2

Chromaticity of the Prepared HDI Homopolymers (Hazen)

| Conversion Rate | Example 1 | Example 2 | Example 3 | Example 4 | Example 5 | Example 6 | Comparative Example 1 | Comparative Example 2 |
|---|---|---|---|---|---|---|---|---|
| 20% | 26 | 27 | 24 | 22 | 21 | 23 | 32 | 37 |
| 30% | 29 | 31 | 27 | 24 | 24 | 25 | 35 | 45 |
| 45% | 32 | 34 | 31 | 29 | 27 | 31 | 38 | 49 |
| 60% | 36 | 37 | 35 | 32 | 31 | 33 | 43 | 57 |

Chromaticities of the homopolymers prepared by the catalysts (examples 1-6) of the present invention are obviously lower than those of the comparative examples; furthermore, as the conversion rate increases from 20% to 60%, the increase of chromaticity in examples is obviously smaller than those in the comparative examples.

EXAMPLES 7-12

The general experimental steps of examples 7-12 are as follows:

To a four-necked flask containing 2222 g (10 mol) isophorone diisocyanate (IPDI) at 70° C. was added a certain amount of catalysts with stirring, and timing was started. During the reaction, the temperature was maintained between 70° C. and 100° C., the IPDI was quantified by the gel chromatography to monitor the conversion rate of reaction. Once the required conversion rate was achieved, a certain amount of terminating agent was added to cease the reaction. After the reaction was finished, separation was conducted and a light colored IPDI homopolymer with a high uretdione content was obtained. Detail conditions are listed in table 4.

TABLE 4

Experimental Conditions of Examples 7-12

| | Catalyst | Catalyst Amount (based on the amount of IPDI, mol %) | Using Condition | Solution and Concentration (mol/L) | Terminating Agent | Amount of Terminating Agent (mol) |
|---|---|---|---|---|---|---|
| Example 7 | a | 0.5 | Solid | — | diethyl phosphate | 0.06 |
| Example 8 | b | 1 | Solution | 5 (dichloromethane) | | 0.12 |
| Example 9 | c | 2 | Solution | 4 (dichloromethane) | | 0.24 |
| Example 10 | d | 2 | Solution | 2 (tetrahydrofuran) | | 0.24 |
| Example 11 | e | 3 | Solid | — | | 0.30 |
| Example 12 | f | 4 | Solution | 0.5 (tetrahydrofuran) | | 0.40 |

COMPARATIVE EXAMPLE 3

Referring to the process of CN 101450928, the process is similar to example 7, except using 0.35 mol catalyst h in catalyzing the homopolymerization reaction and 0.35 mol dimethyl phosphate in terminating the reaction.

TABLE 5

U/O Values of the IPDI Homopolymers Prepared in Examples 7-12 and Comparative Examples 3

| | U/O | | | | | | |
|---|---|---|---|---|---|---|---|
| | U/O Values of the Prepared IPDI Homopolymers | | | | | | |
| Conversion rate | Example 7 | Example 8 | Example 9 | Example 10 | Example 11 | Example 12 | Comparative Example 3 |
| 20% | 92.4 | 91.8 | 94.2 | 98.1 | 98.8 | 95.6 | 87.8 |
| 30% | 82.8 | 80.6 | 82.6 | 88.5 | 89.2 | 87.1 | 76.1 |
| 45% | 64.7 | 61.5 | 63.1 | 69.7 | 70.1 | 66.9 | 55.1 |
| 60% | 52.5 | 51.9 | 54.7 | 59.1 | 61.7 | 57.3 | 48.6 |

TABLE 6

Chromaticity of the IPDI Homopolymers Prepared in Examples 7-12 and Comparative Example 3

| | Chromaticity | | | | | | |
|---|---|---|---|---|---|---|---|
| | Chromaticity of the Prepared IPDI Homopolymers (Hazen) | | | | | | |
| Conversion Rate | Example 7 | Example 8 | Example 9 | Example 10 | Example 11 | Example 12 | Comparative Example 3 |
| 20% | 20 | 21 | 20 | 20 | 19 | 21 | 26 |
| 30% | 22 | 23 | 22 | 22 | 21 | 22 | 28 |
| 45% | 24 | 25 | 24 | 23 | 23 | 24 | 30 |
| 60% | 26 | 28 | 26 | 25 | 24 | 26 | 33 |

EXAMPLE 13

0.01 mol Catalyst a and 0.1 mol catalyst e were added into 25 ml dichloromethane, after totally dissolved, prepare a mixed-catalyst-solution m for later use. 1680 g (10 mol) Hexamethylene-1,6-diisocyanate (HDI) was placed in a four-necked flask at 60° C. with stirring, and timing was started. During the reaction, the temperature was maintained between 60° C. to 67° C., the HDI was quantified with gel chromatography to monitor the conversion rate of reaction. Once the required conversion was achieved, 0.12 mol diethyl phosphate was added to terminate the reaction. After the reaction was finished, separation was conducted and a light colored HDI homopolymer with a high uretdione content was obtained.

TABLE 7

U/O Values and Product's Chromaticity of the HDI Homopolymers Prepared in Example 13

| Conversion Rate of HDI | U/O Value | Product's Chromaticity/Hazen |
|---|---|---|
| 20% | 56.1 | 22 |
| 30% | 45.8 | 25 |
| 45% | 36.5 | 28 |
| 60% | 23.9 | 32 |

When a combination of several catalysts of the present invention was applied, the prepared HDI homopolymer have a lower chromaticity; and the increase of chromaticity is obviously smaller when the conversion rate increases from 20% to 60%.

The invention claimed is:

1. A process for preparing isocyanate homopolymers containing uretdione groups comprising:

in the presence of catalysts, homopolymerizing raw isocyanate monomers to prepare isocyanate homopolymers containing uretdione groups, wherein the catalysts comprise phosphinoboron compounds of the structure of formula (I):

wherein $R_1$, $R_2$ and $R_3$ are independently selected from linear or branched $C_1$-$C_{20}$ alkyl group, optionally substituted $C_3$-$C_{20}$ cycloalkyl group, optionally substituted $C_7$-$C_{15}$ aralkyl or optionally substituted $C_6$-$C_{12}$ aryl group.

2. The process according to claim 1, wherein the phosphinoboron compound catalysts of formula (I) are selected from the group consisting of:

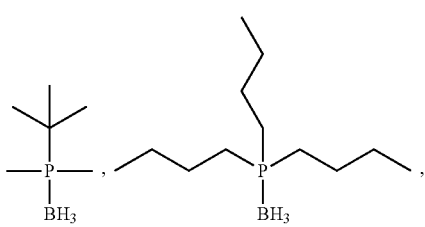

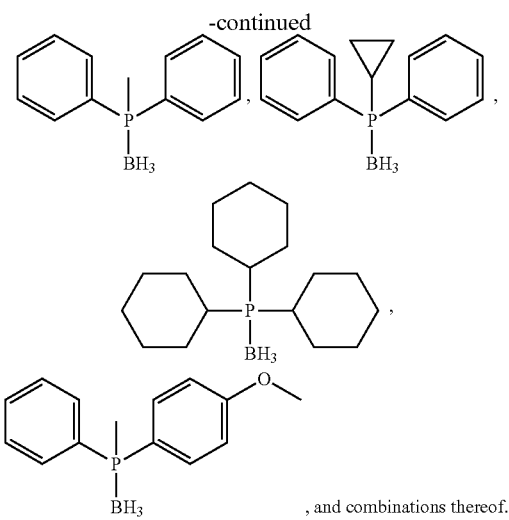
, and combinations thereof.

3. The process according to claim 1, wherein the raw isocyanate monomer is selected from one of the following compounds: aliphatic isocyanate, cycloaliphatic isocyanate or aromatic isocyanate; wherein the isocyanate having a NCO functionality ≥2.

4. The process according to claim 3, wherein the isocyanates are selected from the following compounds: tetramethylene-1,4-diisocyanate, pentamethylene-1,5-diisocyanate, hexamethylene-1,6-diisocyanate, lysine diisocyanate, isophorone diisocyanate, trimethylhexamethylene diisocyanate, dicyclohexylmethane diisocyanate, norbornane dimethylene isocyanate, diphenylmethane diisocyanate, toluene diisocyanate or p-phenyl diisocyanate.

5. The process according to claim 1, wherein the amount of phosphinoboron compound catalysts of formula (I) is 0.1-4 mol %, based on the amount of raw isocyanate monomers.

6. The process according to claim 5, wherein the phosphinoboron compound catalysts of formula (I) are used solely or as a formulated solution, wherein the concentration of the solution is 0.5-5 mol/L.

7. The process according to claim 6, wherein the solvents used in formulating the solution from the phosphinoboron compound catalysts are free of an active hydrogen.

8. The process according to claim 1, wherein the temperature of homopolymerization reaction is 20-120° C.

9. The process according to claim 1, wherein, when the conversion rate of the raw isocyanate monomers in the homopolymerization reaction reaches 20%-60% based on the mass of raw isocyanate monomers, a catalyst poison is used to terminate the homopolymerization reaction.

10. The process according to claim 9, wherein the catalyst poisons are alkylating agents or phosphate esters, where a mole ratio of the catalyst poison to the phosphinoboron compound catalyst is 1:1-2:1.

11. The process according to claim 1, wherein $R_1$, $R_2$ and $R_3$ are independently selected from methyl, linear or branched $C_3$-$C_{20}$ alkyl, alkyl-substituted $C_3$-$C_{20}$ cycloalkyl group, alkyl-substituted $C_7$-$C_{15}$ aralkyl group, alkyl-substituted $C_6$-$C_{12}$ aryl group or alkoxyl-substituted $C_6$-$C_{12}$ aryl group.

12. The process according to claim 1, wherein $R_1$, $R_2$ and $R_3$ are independently selected from methyl, n-butyl, tert-butyl, cyclopropyl, cyclohexyl, phenyl or methoxyphenyl.

13. The process according to claim 4, wherein the isocyanate is selected from hexamethylene-1,6-diisocyanate or isophorone diisocyanate.

14. The process according to claim 5, wherein the amount of phosphinoboron compound catalysts of formula (I) is 0.5-2 mol %, based on the amount of raw isocyanate monomers.

15. The process according to claim 6, wherein the phosphinoboron compound catalysts of formula (I) are used solely or as a formulated solution, wherein the concentration of the solution is 2-4 mol/L.

16. The process according to claim 7, wherein the solvents used in formulating the solution from the phosphinoboron compound catalysts are selected from the group consisting of: halogenated hydrocarbons, aromatic hydrocarbons, ethers, and combinations thereof.

17. The process according to claim 16, wherein the solvents used in formulating the solution from the phosphinoboron compound catalysts are selected from the group consisting of: dichloromethane, tetrahydrofuran, methylbenzene, dimethylbenzene, chlorobenzene, and combinations thereof.

18. The process according to claim 8, wherein the temperature of homopolymerization reaction is 50-100° C.

19. The process according to claim 10, wherein the catalyst poisons are alkylating agents or phosphate esters, where a mole ratio of the catalyst poison to the phosphinoboron compound catalyst is 1:1-1.2:1.

* * * * *